US009236574B2

(12) United States Patent
Wang et al.

(10) Patent No.: US 9,236,574 B2
(45) Date of Patent: Jan. 12, 2016

(54) DINAPHTO[2,3-A:2'3'-H]PHENAZINES AND THEIR USE AS ORGANIC SEMICONDUCTORS

(75) Inventors: Changsheng Wang, Durham (GB); William Mitchell, Chandler's Ford (GB); Mansoor D'Lavari, Bude (GB); Steven Tierney, Southampton (GB)

(73) Assignee: MERCK PATENT GMBH, Darmstadt (DE)

( * ) Notice: Subject to any disclaimer, the term of this patent is extended or adjusted under 35 U.S.C. 154(b) by 190 days.

(21) Appl. No.: 14/004,566

(22) PCT Filed: Feb. 11, 2012

(86) PCT No.: PCT/EP2012/000618
§ 371 (c)(1),
(2), (4) Date: Sep. 11, 2013

(87) PCT Pub. No.: WO2012/123058
PCT Pub. Date: Sep. 20, 2012

(65) Prior Publication Data
US 2014/0008583 A1    Jan. 9, 2014

(30) Foreign Application Priority Data
Mar. 11, 2011    (EP) ..................................... 11002022

(51) Int. Cl.
*C07F 7/08* (2006.01)
*H01L 51/00* (2006.01)
(52) U.S. Cl.
CPC .......... *H01L 51/0094* (2013.01); *C07F 7/0812* (2013.01)
(58) Field of Classification Search
CPC ......... C07F 7/08; C07F 7/0812; H01L 51/00; H01L 51/0094
USPC ................... 252/500; 544/229, 114, 115, 120
See application file for complete search history.

(56) References Cited

U.S. PATENT DOCUMENTS

| 1,970,654 | A | * | 8/1934 | Hooley et al. | 544/340 |
| 2,019,530 | A | * | 11/1935 | Whyte Fairweather et al. | 544/340 |
| 2,041,402 | A | * | 5/1936 | Whyte Fairweather et al. | 544/340 |
| 2,063,594 | A | * | 12/1936 | Whyte Fairweather et al. | 544/340 |
| 2,091,143 | A | * | 8/1937 | Whyte Fairweather | 8/651 |
| 2,200,480 | A | * | 5/1940 | Stallmann | 544/340 |

FOREIGN PATENT DOCUMENTS

| JP | 2008 098453 | 4/2008 | |
| WO | WO-2007 020442 | 2/2007 | |
| WO | WO-2010 108978 | 9/2010 | |
| WO | WO 2012100900 A1 * | 8/2012 | ............ C07F 7/0812 |

OTHER PUBLICATIONS

International Search Report for PCT/EP2012/000618, Date of the actual completion of the search report: Mar. 9, 2012, Date of mailing of the international search report: Mar. 28, 2012.
Timofei, S. et al., "Structure-Affinity Binding Relationships by Principle-Component-Regression Analysis of Anthraquinone Dyes," Quant. Struct. Act. Relat., 1995, vol. 14, pp. 444-449.
Toyo Ink MFG CO Ltd., "Organic Transistor," Patent Abstracts of Japan, Publication Date: Apr. 24, 2008; English Abstract of JP-2008 098453.

* cited by examiner

*Primary Examiner* — Douglas McGinty
(74) *Attorney, Agent, or Firm* — Millen White Zelano and Branigan, PC; Csaba Henter; Anthony Zelano

(57) ABSTRACT

The invention relates to novel dinaphtho[2,3-a:2',3'-h]phenazine compounds, to methods for their preparation and intermediates used therein, formulations comprising them, the use of these compounds and formulations as semiconductor material in organic electronic (OE) devices, and OE devices comprising these compounds and formulations.

17 Claims, No Drawings

DINAPHTO[2,3-A:2'3'-H]PHENAZINES AND THEIR USE AS ORGANIC SEMICONDUCTORS

FIELD OF THE INVENTION

The invention relates to novel dinaphtho[2,3-a:2',3'-h] phenazine compounds, to methods for their preparation and intermediates used therein, formulations comprising them, the use of these compounds and formulations as semiconductor material in organic electronic (OE) devices, and OE devices comprising these compounds and formulations.

BACKGROUND AND PRIOR ART

Organic semiconductors (OSCs) are expected to revolutionise the manufacturing process of the thin film field-effect transistors (TFTs) used for display technologies. Compared with the classical Si based field-effect transistor (FETs), organic TFTs can be fabricated much more cost-effectively by solution coating methods such as spin-coating, drop casting, dip-coating, and more efficiently, ink-jet printing. Solution processing of OSCs requires the molecular materials to be 1) soluble enough in non-toxic solvents; 2) stable in the solution state; 3) easy to crystallise when solvents are evaporated; and most importantly, 4) to provide high charge carrier mobilities with low off currents. In this context, pentacenes and hetero-acenes with solublising substituents have shown to be promising classes of p-type OSC materials. Notably, unsymmetrically substituted pentacene derivatives have shown hole mobility greater than 3 $cm^2/Vs$, as disclosed in WO 2009/155106 A1 while fluorinated anthracenodithiophene derivatives (F-ADTs) have shown hole mobility greater than 1 $cm^2/Vs$, as disclosed in US2008/0128680 A1; Payne et al., *J. Am. Chem. Soc.*, 2005, 127 (14), 4986; and Subramanian et al., *J. Am. Chem. Soc.* 2008, 130(9), 2706-2707.

However, the currently available materials still have some major drawbacks, like a low photo and environment stability particularly in solution states, and a low temperature of the phase transition and melting point. Also for future OLED backplane applications, which demand higher source and drain current, the mobility and processibility of currently available materials needs further improvement.

Acenes larger than pentacene keep attracting interests in the quest for novel OSCs due to the predicted lower reorganization energy (see Deng et al., *J. Phys. Chem. B*, 2004, 108, 8614) and the potential higher charge carrier mobility (see Cheng et al., *J. Chem. Phys.*, 2003, 118, 3764). However, linear elongation of the aromatic cores by fusing additional benzene rings is witnessed by the decreased stability and solubility in organic solvents, which compromised the practical application of these analogues as OSC materials (see Purushothaman et al., *Org. Lett.*, 2010, 12(9), 2060). Interestingly, polycyclic aromatic hydrocarbons much larger than pentacene have either been synthesized as nano materials (see Yang et al., *J. Am. Chem. Soc.*, 2008, 130 (13), 4216) or existed in nature as dye stuffs without stability issues due to their 2-D fusing features. This type of structure is most notably represented by free-standing graphene, a class of intrinsic 2-D polycyclic aromatic system, of which large charge carrier mobilities exceeding $10^4$ $cm^2/Vs$ have been observed under ambient conditions (see Geim et al., *Nat. Mater.*, 2007, 6(3), 183; Allen et al., *Chem. Rev.*, 2010, 110(1), 132), and exceeding $2\times10^5$ $cm^2/Vs$ have been achieved under optimised conditions (see Bolotin et al., *Solid State Commun.*, 2008, 146, 351).

Therefore, there is still a great need for new OSC materials that show good electronic properties, especially high charge carrier mobility, good processibilty and high thermal and environmental stability, especially a high solubility in organic solvents.

It was an aim of the present invention to provide compounds for use as organic semiconducting materials that do not have the drawbacks of prior art materials as described above, and do especially show good electronic properties, especially high charge carrier mobility, good processibilty and high thermal and environmental stability, especially a high solubility in organic solvents. Another aim of the invention was to extend the pool of organic semiconducting materials available to the expert.

It was found that these aims can be achieved by providing compounds as claimed in the present invention. These compounds are based on indanthrone, a industrially available dye stuff with a kinked polycyclic aromatic ring structure as shown below, as the starting material.

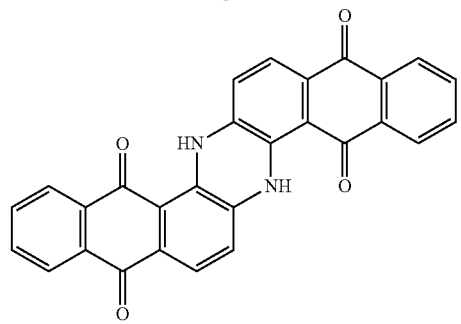 [SMILES: O=c1c2ccccc2c(=O)c2c1ccc1[nH]c3c(ccc4c(=O)c5ccccc5c(=O)c43)[nH]c12]

For the purposes of the present invention, this indanthrone has been made soluble in organic solvents, so that it becomes solution processible, by the introduction of solublising functional groups through aromatisation of its quinoid structure into a new core unit, i.e. dinaphtho[2,3-a:2',3'-h]phenazine (hereinafter also shortly referred to as "indanthrene"). The inventors of the present invention have found that these indanthrene derivatives exhibit high solubility in organic solvents, especially those that are typically used in organic electronic device manufacture, and in addition show good thermal stability and high charge carrier mobilities.

No examples of indanthrene based materials have been reported up to date in the literature.

SUMMARY OF THE INVENTION

The invention relates to compounds of formula I

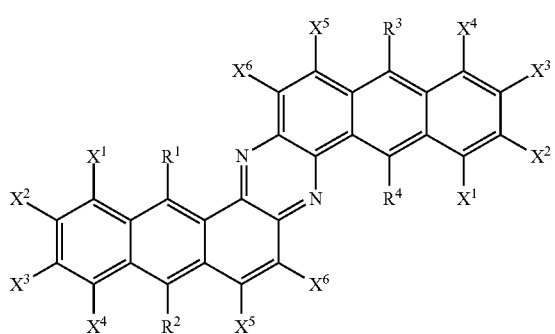

I wherein the individual groups have the following meanings
R¹ to R⁴ independently of each other denote straight chain, branched or cyclic alkyl with 1 to 40 C-atoms, which is unsubstituted or substituted by one or more groups L, and wherein one or more non-adjacent CH₂ groups are optionally replaced, in each case independently from one another, by —O—, —S—, —NR⁰—, —SiR⁰R⁰⁰—, —CY⁰=CY⁰⁰— or —C≡C— in such a manner that O and/or S atoms are not linked directly to one another, or denote aryl or heteroaryl with 4 to 20 ring atoms which is unsubstituted or substituted by one or more groups L, X¹ to X⁶ independently of each other, and on each occurrence identically or differently, denote H or have one of the meanings given for L, L is selected from P-Sp-, F, Cl, Br, I, —OH, —CN, —NO₂, —NCO, —NCS, —OCN, —SCN, —C(=O)NR⁰R⁰⁰, —C(=O)X⁰, —C(=O)R⁰, —NR⁰R⁰⁰, C(=O)OH, optionally substituted silyl or germyl, optionally substituted aryl or heteroaryl having 4 to 20 ring atoms, straight chain, branched or cyclic alkyl, alkoxy, oxaalkyl or thioalkyl with 1 to 30, preferably 1 to 12 C atoms which is unsubstituted or substituted with one or more F or Cl atoms or OH groups, and straight chain, branched or cyclic alkenyl, alkynyl, alkylcarbonyl, alkoxycarbonyl, alkylcarbonyloxy or alkoxycarbonyloxy with 2 to 20, preferably 2 to 12 C atoms which is unsubstituted or substituted with one or more F or Cl atoms or OH groups, P is a polymerisable group, Sp is a spacer group or a single bond, X⁰ is halogen, R⁰ and R⁰⁰ independently of each other denote H or alkyl with 1 to 20 C-atoms, Y⁰ and Y⁰⁰ independently of each other denote H, F, Cl or CN.

The invention further relates to a formulation comprising one or more compounds of formula I and one or more solvents, preferably selected from organic solvents.

The invention further relates to an organic semiconducting formulation comprising one or more compounds of formula I, one or more organic binders, or precursors thereof, preferably having a permittivity ∈ at 1,000 Hz and 20° C. of 3.3 or less, and optionally one or more solvents.

The invention further relates to the use of compounds and formulations according to the present invention as charge transport, semiconducting, electrically conducting, photoconducting or light emitting material in an optical, electrooptical, electronic, electroluminescent or photoluminescent component or device.

The invention further relates to a charge transport, semiconducting, electrically conducting, photoconducting or light emitting material or component comprising one or more compounds or formulations according to the present invention.

The invention further relates to an optical, electrooptical or electronic component or device comprising one or more compounds, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, photodiodes, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

This invention relates to a new class of compounds expressed by the general structure as shown in formula I. Apart from being novel, these compounds demonstrate one or more of the following properties:

i) They show good semiconducting properties, especially high charge carrier mobilities and low off-current values in field-effect transistors.

ii) They exhibit excellent photo and thermal stabilities in both solid and solution states.

iii) They have good solubility in non-toxic organic solvents, which allows them to be solution processible.

The compounds of the present invention are easy to synthesize and exhibit several advantageous properties, like a high charge carrier mobility, a high melting point, a high solubility in organic solvents, a good processability for the device manufacture process, a high oxidative and photostability and a long lifetime in electronic devices. In addition, they show advantageous properties as discussed above and below.

Preferably R¹, R², R³ and R⁴ in formula I have the same meaning.

Very preferred are compounds of formula I wherein R¹⁻⁴ independently of each other denote —C≡C—R⁵, wherein R⁵ is an optionally substituted silyl or germyl group, or an alkyl, aryl or heteroaryl group with 4 to 20 ring atoms which is unsubstituted or substituted by one or more groups L as defined above.

If R⁵ or L is an optionally substituted alkyl, silyl or germyl group, it is preferably selected of the formula II

-AR'R"R'''    II wherein

A is C, Si or Ge, preferably Si, and

R', R", R''' are identical or different groups selected from the group consisting of H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L', and L' has one of the meanings given for L in formula I, which is different from a silyl and germyl group.

Preferably in the compounds of formula I R¹⁻⁴ denote —C≡C—R⁵, wherein all groups R⁵ denote identical groups ARR'R" of formula II.

A in formula II is preferably Si.

Preferably, R', R" and R''' in the groups of formula II are independently of each other selected from optionally substituted and straight-chain alkyl or alkoxy having 1 to 20 C atoms, which is for example methyl, ethyl, n-propyl, methoxy or ethoxy, optionally substituted and branched alkyl or alkoxy having 3 to 20 C atoms, which is for example isopropyl or t-butyl, optionally substituted and cyclic alkyl or alkoxy having 3 to 20 C atoms, which is for example cyclopropyl, 2,3-dimethylcyclopropyl, 2,2,3,3-tetramethylcyclopropyl, cyclobutyl, cyclopentyl, optionally substituted and straight-chain, branched or cyclic alkenyl, alkynyl or alkylcarbonyl having 2 to 20 C atoms, which is for example allyl, isopropenyl, 2-but-1-enyl, cis-2-but-2-enyl, 3-but-1-enyl, propynyl or acetyl, optionally substituted aryl, heteroaryl, arylalkyl or heteroarylalkyl, aryloxy or heteroaryloxy having 5 to 10 ring atoms, which is for example phenyl, p-tolyl, benzyl, 2-furanyl, 2-thienyl, 2-selenophenyl, N-methylpyrrol-2-yl or phenoxy.

Further preferred is a group ARR'R" of formula II wherein one or more of R', R" and R'" together with the Si or Ge atom form a cyclic group, preferably having 2 to 8 C atoms.

In another preferred embodiment, in the groups ARR'R" of formula II all substituents R, R' and R" are identical.

In another preferred embodiment, in the groups ARR'R" of formula II at least two of the substituents R, R' and R" are not identical. This means that at least one substituent R, R' and R" has a meaning that is different from the meanings of the other substituents R, R' and R.

In another preferred embodiment, in the groups ARR'R" of formula II each of R, R' and R" has a meaning that is different from the other of R' and R". Further preferred are groups ARR'R" of formula II wherein two of R, R' and R" have the same meaning and one of R, R' and R" has a meaning which is different from the other two of R, R' and R".

Further preferred are groups ARR'R" of formula II, wherein one or more, very preferably one or two, of R, R' and R" denote or contain an optionally substituted alkenyl group having 2 to 20 C atoms or an optionally substituted aryl or heteroaryl group having 5 to 10 ring atoms.

Further preferred are groups ARR'R" of formula II, wherein one or two of R, R' and R" denote optionally substituted cyclic alkyl having 3 to 20 C atoms or optionally substituted alkenyl having 2 to 20 C atoms, and the others denote straight-chain alkyl having 1 to 20 C atoms or branched alkyl having 3 to 10 C atoms, like for example cyclopentyldiethylsilyl.

Further preferred are groups ARR'R" of formula II, wherein all of R, R' and R" denote identical or different, optionally substituted straight-chain alkyl having 1 to 20 C atoms or optionally substituted branched alkyl having 3 to 10 C atoms, like for example triethylsilyl or triisopropylsilyl.

Very preferred are compounds of formula I wherein all of $X^1$ to $X^6$ are H.

In another preferred embodiment, in the compounds of formula I $X^1$, $X^2$, $X^3$, $X^4$, $X^5$ and $X^6$ are selected from the group consisting of H, F, Cl, Br, I, —CN, and straight chain, branched or cyclic alkyl, alkoxy, thioalkyl, alkenyl, alkynyl, alkylcarbonyl, alkoxycarbonyl, alkylcarbonyloxy, alkylcarbonylamido, alkylamidocarbonyl or alkoxycarbonyloxy with 1 to 20, preferably 1 to 12 C atoms which is unsubstituted or substituted with one or more F or Cl atoms or OH groups or perfluorinated.

In another preferred embodiment, in the compounds of formula I one or more of $X^1$, $X^2$, $X^3$, $X^4$, $X^5$ and $X^6$ are selected from the group consisting of aromatic and heteroaromatic groups with 4 to 25 ring atoms, which are mono- or polycyclic, i.e. which may also contain two or more individual rings that are connected to each other via single bonds, or contain two or more fused rings, and wherein each ring is unsubstituted or substituted with one or more groups L as defined above.

Very preferably these aforementioned aromatic and heteroaromatic groups are selected from the group consisting of phenyl, furan, thiophene, selenophene, N-pyrrole, pyridine, pyrimidine, thiazole, thiadiazole, oxazole, oxadiazole, selenazole, and bi-, tri- or tetracyclic aryl or heteroaryl groups containing one or more of the aforementioned rings and optionally one or more benzene rings, wherein the individual rings are connected by single bonds or fused with each other, and wherein all the aforementioned groups are unsubstituted, or substituted with one or more groups L as defined above.

Very preferably these aforementioned bi-, tri- or tetracyclic aryl or heteroaryl groups are selected from the group consisting of thieno[3,2-b]thiophene, dithieno[3,2-b:2',3'-d]thiophene, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b]dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, benzo[b]thiophene, benzo[b]selenophene, benzooxazole, benzothiazole, benzoselenazole, wherein all the aforementioned groups are unsubstituted or substituted with one or more groups L as defined above.

Preferred compounds of formula I are selected from the following formula:

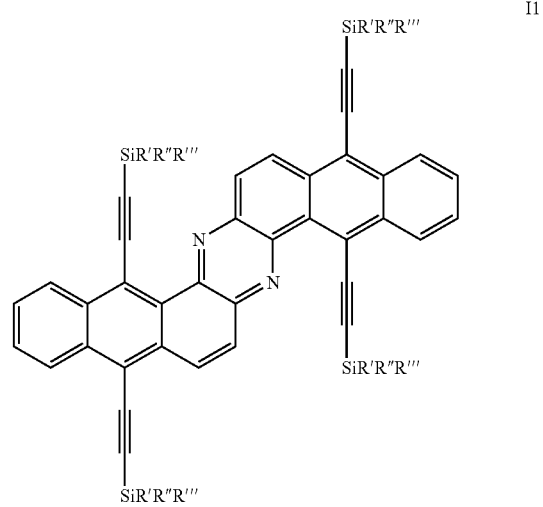

wherein R, R' and R" are as defined in formula II or have one of the preferred meanings as given above and below.

Above and below, an alkyl group or an alkoxy group, i.e. alkyl where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, i.e. alkyl wherein one or more $CH_2$ groups are replaced by —CH═CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5C atoms are generally preferred.

An oxaalkyl group, i.e. alkyl where a non-terminal $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In an alkyl group wherein one $CH_2$ group is replaced by —O— and another $CH_2$ group is replaced by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonyl-methyl, ethoxycarbonylmethyl, propoxycarbonylmethyl, butoxycarbonyl-methyl, 2-(methoxycarbonyl)ethyl, 2-(ethoxycarbonyl)ethyl, 2-(propoxycarbonyl)-ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxymethyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxyheptyl, 8,8-bis-carboxy-octyl, 9,9-bis-carboxy-nonyl, 10,10-bis-carboxydecyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

$R^{1-5}$, R', R" and R'" can be an achiral or a chiral group. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyl-oxy-carbonyl, 2-methylbutyryloxy, 3-methylvaleroyloxy, 4-methylhexanoy-loxy, 2-chlor-propionyloxy, 2-chloro-3-methyl-butyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tertiary butyl, isopropoxy, 2-methylpropoxy and 3-methylbutoxy.

—$CY^o$=$CY^{oo}$— is preferably —CH=CH—, —CF=CF— or —CH=C(CN)—.

Halogen is F, Cl, Br or I, preferably F, Cl, Br.

L is preferably selected from P-Sp-, F, Cl, Br, I, —OH, —CN, —$NO_2$, —NCO, —NCS, —OCN, —SCN, —C(=O)$NR^oR^{oo}$, —C(=O)$X^o$, —C(=O)$R^o$, —$NR^oR^{oo}$, C(=O)OH, straight chain, branched or cyclic alkyl, alkoxy, oxaalkyl or thioalkyl with 1 to 20, preferably 1 to 12 C atoms which is unsubstituted or substituted with one or more F or Cl atoms or OH groups or perfluorinated, and straight chain, branched or cyclic alkenyl, alkynyl, alkylcarbonyl, alkoxycarbonyl, alkylcarbonyloxy or alkoxycarbonyloxy with 2 to 20, preferably 2 to 12 C atoms which is unsubstituted or substituted with one or more F or Cl atoms or OH groups or perfluorinated.

The compounds of formula I may also be substituted with a polymerisable or reactive group, which is optionally protected during the process of forming the polymer. Particularly preferred compounds of this type are those of formula I that contain one or more substituents L which denote P-Sp, wherein P is a polymerisable or reactive group and Sp is a spacer group or a single bond. These compounds are particularly useful as semi-conductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or reactive group P is selected from $CH_2$=$CW^1$—COO—, $CH_2$=$CW^1$—CO—,

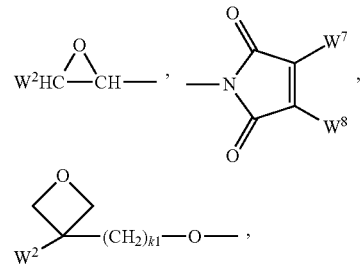

$CH_2$=$CW^2$—(O)$_{k1}$—, $CH_3$—CH=CH—O—, ($CH_2$=CH)$_2$CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—NH—, $CH_2$=$CW^1$—CO—NH—, $CH_2$=CH—(COO)$_{k1}$-Phe-(O)$_{k2}$—, $CH_2$=CH—(CO)$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—COO—, $CH_2$=C($CH_3$)—COO—, $CH_2$=CH—, $CH_2$=CH—O—, $(CH_2$=CH$)_2$CH—OCO—, $(CH_2$=CH$)_2$CH—O—,

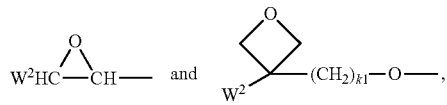

or protected derivatives thereof.

Polymerisation of group P can be carried out according to methods that are known to the ordinary expert and described in the literature, for example in D. J. Broer; G. Challa; G. N. Mol, *Macromol. Chem*, 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—$NR^0$—, —$NR^0$—CO—, —$NR^0$—CO—$NR^{00}$—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^0$=$CY^{00}$—, —C≡C—, —CH=CH—COO—, —OCO—CH=CH— or a single bond, $R^0$ and $R^{00}$ are independently of each other H or alkyl with 1 to 12 C-atoms, and $Y^0$ and $Y^{00}$ are independently of each other H, F, Cl or CN.

X' is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^0$=$CY^{00}$—, —C≡C— or a single bond, in particular —O—, —S—, —C≡C—, —$CY^0$=$CY^{00}$— or a single bond. In another preferred embodiment X' is a group that is able to form a conjugated system, such as —C≡C— or —$CY^0$=$CY^{00}$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^0R^{00}$—O$)_p$—, with p being an integer from 2 to 12, q being an integer from 1 to 3 and $R^0$ and $R^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The compounds of formula I can be synthesized according to or in analogy to methods that are known to the skilled person and are described in the literature. Other methods of preparation can be taken from the examples. Especially preferred and suitable synthesis methods are further described below.

A suitable and preferred synthesis route for a soluble dinaphtho[2,3-a:2',3'-h]phenazine (indanthrene) is exemplarily shown in Scheme 1 below for a indanthrene that is disubstituted with cyclopentyldiethyl-silylethynyl groups.

Indanthrone 1 is oxidised with nitric acid as described in the literature (R. Scholl, H. Berblinger and J. Mansfeld, *Chem. Ber.*, 1907, 40, 320) to yield indanthrenetetraone 2. Treating 2 with lithium cyclopentyldiethyl-silyl-acetylide 3 yields the ethynylated indanthrene tetraol 4. Using a reported procedure (S. Miao, M. D. Smith, and U. H. F. Bunz, *Org. Lett.*, 2006, 8(4), 757), 4 is reductive-aromatized under acidic conditions to afford indanthrene 5

Further derivatives with different substituents can be synthesised in analogous manner.

Scheme 1

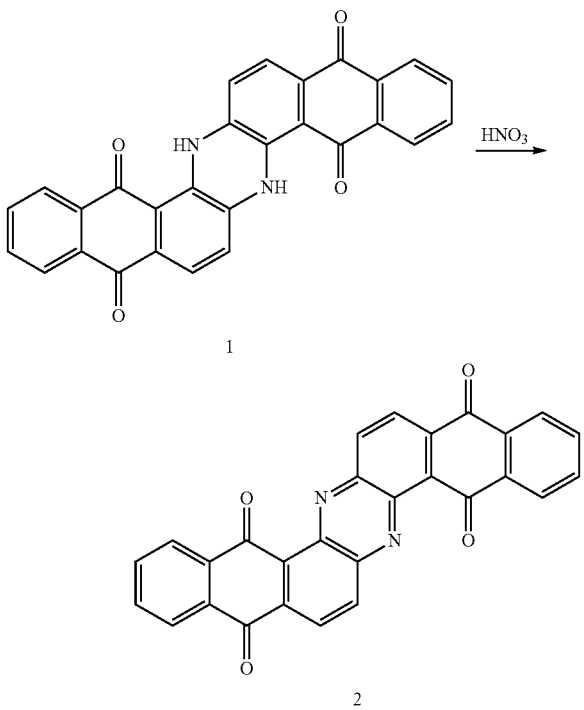

-continued

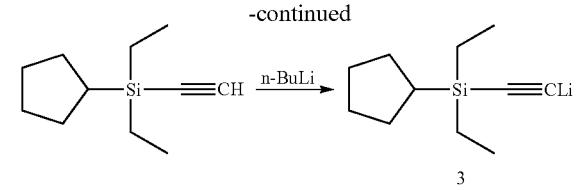

2 + 3 ⟶

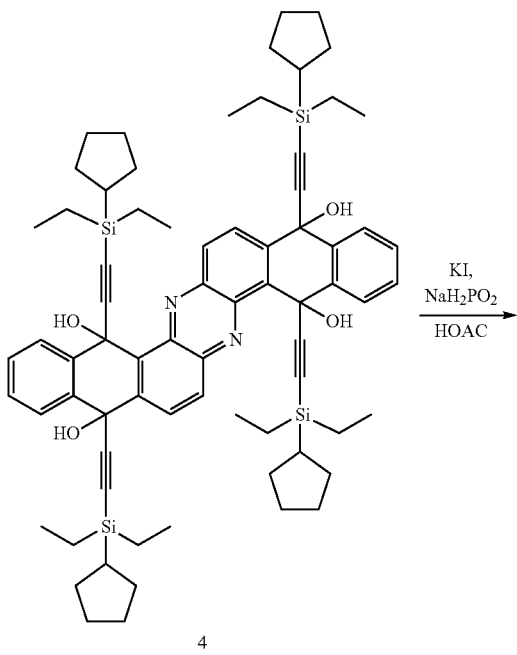

4

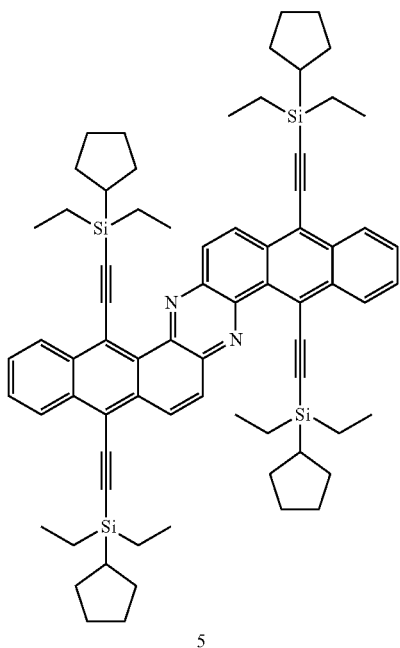 [SMILES: CC[Si](C#Cc1c2ccccc2c(C#C[Si](CC)(CC)C2CCCC2)c2c1ccc1nc3c(ccc4c(C#C[Si](CC)(CC)C5CCCC5)c5ccccc5c(C#C[Si](CC)(CC)C5CCCC5)c43)nc12)(CC)C1CCCC1]

5

The invention further relates to a formulation comprising one or more compounds of formula I and one or more solvents, preferably selected from organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

The invention further relates to an organic semiconducting formulation comprising one or more compounds of formula I, one or more organic binders, or precursors thereof, preferably having a permittivity ∈ at 1,000 Hz of 3.3 or less, and optionally one or more solvents.

Combining specified soluble compounds of formula I, especially compounds of the preferred formulae as described above and below, with an organic binder resin (hereinafter also referred to as "the binder") results in little or no reduction in charge mobility of the compounds of formula I, even an increase in some instances. For instance, the compounds of formula I may be dissolved in a binder resin (for example poly(α-methyl-styrene)) and deposited (for example by spin coating), to form an organic semiconducting layer yielding a high charge mobility. Moreover, a semi-conducting layer formed thereby exhibits excellent film forming characteristics and is particularly stable.

If an organic semiconducting layer formulation of high mobility is obtained by combining a compound of formula I with a binder, the resulting formulation leads to several advantages. For example, since the compounds of formula I are soluble they may be deposited in a liquid form, for example from solution. With the additional use of the binder the formulation can be coated onto a large area in a highly uniform manner.

Furthermore, when a binder is used in the formulation it is possible to control the properties of the formulation to adjust to printing processes, for example viscosity, solid content, surface tension. Whilst not wishing to be bound by any particular theory it is also anticipated that the use of a binder in the formulation fills in volume between crystalline grains otherwise being void, making the organic semiconducting layer less sensitive to air and moisture. For example, layers formed according to the process of the present invention show very good stability in OFET devices in air.

The invention also provides an organic semiconducting layer which comprises the organic semiconducting layer formulation.

The invention further provides a process for preparing an organic semiconducting layer, said process comprising the following steps:

(i) depositing on a substrate a liquid layer of a formulation comprising one or more compounds of formula I as described above and below, one or more organic binder resins or precursors thereof, and optionally one or more solvents,
(ii) forming from the liquid layer a solid layer which is the organic semiconducting layer,
(iii) optionally removing the layer from the substrate.

The process is described in more detail below.

The invention additionally provides an electronic device comprising the said organic semiconducting layer. The electronic device may include, without limitation, an organic field effect transistor (OFET), organic light emitting diode (OLED), photodetector, sensor, logic circuit, memory element, capacitor or photovoltaic (PV) cell. For example, the active semiconductor channel between the drain and source in an OFET may comprise the layer of the invention. As another example, a charge (hole or electron) injection or transport layer in an OLED device may comprise the layer of the invention. The formulations according to the present invention and layers formed therefrom have particular utility in OFETs especially in relation to the preferred embodiments described herein.

The semiconducting compound of formula I preferably has a charge carrier mobility, μ, of more than 0.001 $cm^2V^{-1}s^{-1}$, very preferably of more than 0.01 $cm^2V^{-1}s^{-1}$, especially preferably of more than 0.1 $cm^2V^{-1}s^{-1}$ and most preferably of more than 0.5 $cm^2V^{-1}s^{-1}$.

The binder, which is typically a polymer, may comprise either an insulating binder or a semiconducting binder, or mixtures thereof may be referred to herein as the organic binder, the polymeric binder or simply the binder.

Preferred binders according to the present invention are materials of low permittivity, that is, those having a permittivity $\in$ of 3.3 or less. The organic binder preferably has a permittivity $\in$ of 3.0 or less, more preferably 2.9 or less. Preferably the organic binder has a permittivity $\in$ at of 1.7 or more. It is especially preferred that the permittivity of the binder is in the range from 2.0 to 2.9. Whilst not wishing to be bound by any particular theory it is believed that the use of binders with a permittivity $\in$ of greater than 3.3, may lead to a reduction in the OSC layer mobility in an electronic device, for example an OFET. In addition, high permittivity binders could also result in increased current hysteresis of the device, which is undesirable.

An example of a suitable organic binder is polystyrene. Further examples of suitable binders are disclosed for example in US 2007/0102696 A1. Especailly suitable and preferred binders are described in the following.

In one type of preferred embodiment, the organic binder is one in which at least 95%, more preferably at least 98% and especially all of the atoms consist of hydrogen, fluorine and carbon atoms.

It is preferred that the binder normally contains conjugated bonds, especially conjugated double bonds and/or aromatic rings.

The binder should preferably be capable of forming a film, more preferably a flexible film. Polymers of styrene and a-methyl styrene, for example copolymers including styrene, a-methylstyrene and butadiene may suitably be used.

Binders of low permittivity of use in the present invention have few permanent dipoles which could otherwise lead to random fluctuations in molecular site energies. The permittivity $\in$ (dielectric constant) can be determined by the ASTM D150 test method. The permittivity values given above and below, unless stated otherwise, refer to 1,000 Hz and 20° C.

It is also preferred that in the present invention binders are used which have solubility parameters with low polar and hydrogen bonding contributions as materials of this type have low permanent dipoles. A preferred range for the solubility parameters ('Hansen parameter') of a binder for use in accordance with the present invention is provided in Table 1 below.

TABLE 1

|  | Hansen parameter | | |
| --- | --- | --- | --- |
|  | $\delta_d$ $MPa^{1/2}$ | $\delta_p$ $MPa^{1/2}$ | $\delta_h$ $MPa^{1/2}$ |
| Preferred range | 14.5+ | 0-10 | 0-14 |
| More preferred range | 16+ | 0-9 | 0-12 |
| Most preferred range | 17+ | 0-8 | 0-10 |

The three dimensional solubility parameters listed above include: dispersive ($\delta_d$), polar ($\delta_p$) and hydrogen bonding ($\delta_h$) components (C. M. Hansen, Ind. Eng. and Chem., Prod. Res. and Devl., 9, No 3, p 282., 1970). These parameters may be determined empirically or calculated from known molar group contributions as described in Handbook of Solubility Parameters and Other Cohesion Parameters ed. A. F. M. Barton, CRC Press, 1991. The solubility parameters of many known polymers are also listed in this publication.

It is desirable that the permittivity of the binder has little dependence on frequency. This is typical of non-polar materials. Polymers and/or copolymers can be chosen as the binder by the permittivity of their substituent groups. A list of suitable and preferred low polarity binders is given (without limiting to these examples) in Table 2:

TABLE 2

| Binder | typical low frequency permittivity (ϵ) |
| --- | --- |
| polystyrene | 2.5 |
| poly(α-methylstyrene) | 2.6 |
| poly(α-vinylnaphtalene) | 2.6 |
| poly(vinyltoluene) | 2.6 |
| polyethylene | 2.2-2.3 |
| cis-polybutadiene | 2.0 |
| polypropylene | 2.2 |
| poly(4-methyl-1-pentene) | 2.1 |
| poly (4-methylstyrene) | 2.7 |
| poly(chorotrifluoroethylene) | 2.3-2.8 |
| poly(2-methyl-1,3-butadiene) | 2.4 |
| poly(p-xylylene) | 2.6 |
| poly(α-α-α'-α' tetrafluoro-p-xylylene) | 2.4 |
| poly[1,1-(2-methyl propane)bis(4-phenyl)carbonate] | 2.3 |
| poly(cyclohexyl methacrylate) | 2.5 |
| poly(chlorostyrene) | 2.6 |
| poly(2,6-dimethyl-1,4-phenylene ether) | 2.6 |
| polyisobutylene | 2.2 |
| poly(vinyl cyclohexane) | 2.2 |
| poly(vinylcinnamate) | 2.9 |
| poly(4-vinylbiphenyl) | 2.7 |

Further preferred binders are poly(1,3-butadiene) and polyphenylene.

Especially preferred are formulations wherein the binder is selected from poly-α-methyl styrene, polystyrene and poly-triarylamine or any copolymers of these, and the solvent is selected from xylene(s), toluene, tetralin and cyclohexanone.

Copolymers containing the repeat units of the above polymers are also suitable as binders. Copolymers offer the possibility of improving compatibility with the compounds of formula I, modifying the morphology and/or the glass transition temperature of the final layer composition. It will be appreciated that in the above table certain materials are insoluble in commonly used solvents for preparing the layer. In these cases analogues can be used as copolymers. Some examples of copolymers are given in Table 3 (without limiting to these examples). Both random or block copolymers can be used. It is also possible to add more polar monomer components as long as the overall composition remains low in polarity.

TABLE 3

| Binder | typical low frequency permittivity ($\epsilon$) |
|---|---|
| poly(ethylene/tetrafluoroethylene) | 2.6 |
| poly(ethylene/chlorotrifluoroethylene) | 2.3 |
| fluorinated ethylene/propylene copolymer | 2-2.5 |
| polystyrene-co-α-methylstyrene | 2.5-2.6 |
| ethylene/ethyl acrylate copolymer | 2.8 |
| poly(styrene/10% butadiene) | 2.6 |
| poly(styrene/15% butadiene) | 2.6 |
| poly(styrene/2,4 dimethylstyrene) | 2.5 |
| Topas ™ (all grades) | 2.2-2.3 |

Other copolymers may include: branched or non-branched polystyrene-block-polybutadiene, polystyrene-block(polyethylene-ran-butylene)-block-polystyrene, polystyrene-block-polybutadiene-block-polystyrene, poly-styrene-(ethylene-propylene)-diblock-copolymers (e.g. KRATON®-G1701E, Shell), poly(propylene-co-ethylene) and poly(styrene-co-methylmethacrylate).

Preferred insulating binders for use in the organic semiconductor layer formulation according to the present invention are poly(α-methylstyrene), polyvinylcinnamate, poly(4-vinylbiphenyl), poly(4-methylstyrene), and Topas™8007 (linear olefin, cyclo-olefin(norbornene) copolymer available from Ticona, Germany). Most preferred insulating binders are poly(α-methylstyrene), polyvinylcinnamate and poly(4-vinylbiphenyl).

The binder can also be selected from crosslinkable binders, like e.g. acrylates, epoxies, vinylethers, thiolenes etc., preferably having a sufficiently low permittivity, very preferably of 3.3 or less. The binder can also be mesogenic or liquid crystalline.

As mentioned above the organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility, $\mu$, of at least $10^{-5}$ cm$^2$V$^{-1}$s$^{-1}$, more preferably at least $10^{-4}$ cm$^2$V$^{-1}$s$^{-1}$.

A preferred class of semiconducting binder is a polymer as disclosed in U.S. Pat. No. 6,630,566, preferably an oligomer or polymer having repeat units of formula 1:

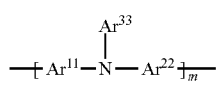

wherein
Ar$^{11}$, Ar$^{22}$ and Ar$^{33}$ which may be the same or different, denote, independently if in different repeat units, an optionally substituted aromatic group that is mononuclear or polynuclear, and m is an integer ≥1, preferably ≥6, preferably ≥10, more preferably ≥15 and most preferably ≥20.

In the context of Ar$^{11}$, Ar$^{22}$ and Ar$^{33}$, a mononuclear aromatic group has only one aromatic ring, for example phenyl or phenylene. A polynuclear aromatic group has two or more aromatic rings which may be fused (for example naphthyl or naphthylene), individually covalently linked (for example biphenyl) and/or a combination of both fused and individually linked aromatic rings. Preferably each Ar$^{11}$, Ar$^{22}$ and Ar$^{33}$ is an aromatic group which is substantially conjugated over substantially the whole group.

Further preferred classes of semiconducting binders are those containing substantially conjugated repeat units. The semiconducting binder polymer may be a homopolymer or copolymer (including a block-copolymer) of the general formula 2:

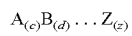

wherein A, B, ..., Z each represent a monomer unit and (c), (d), ... (z) each represent the mole fraction of the respective monomer unit in the polymer, that is each (c), (d), ... (z) is a value from 0 to 1 and the total of (c)+(d)+ ... +(z)=1.

Examples of suitable and preferred monomer units A, B, ... Z include units of formula 1 above and of formulae 3 to 8 given below (wherein m is as defined in formula 1:

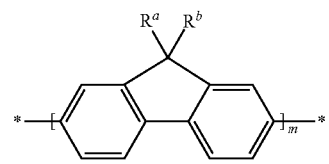

wherein
R$^a$ and R$^b$ are independently of each other selected from H, F, CN, NO$_2$, —N(R$^c$)(R$^d$) or optionally substituted alkyl, alkoxy, thioalkyl, acyl, aryl,
R$^c$ and R$^d$ are independently or each other selected from H, optionally substituted alkyl, aryl, alkoxy or polyalkoxy or other substituents,
and wherein the asterisk (*) is any terminal or end capping group including H, and the alkyl and aryl groups are optionally fluorinated;

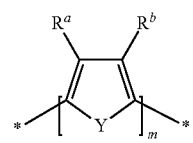

wherein
Y is Se, Te, O, S or —N(R$^e$), preferably O, S or —N(R$^e$)—,
R$^e$ is H, optionally substituted alkyl or aryl,
R$^a$ and R$^b$ are as defined in formula 3;

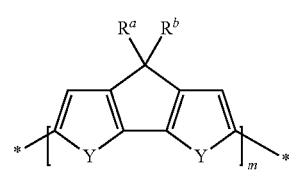

wherein $R^a$, $R^b$ and Y are as defined in formulae 3 and 4;

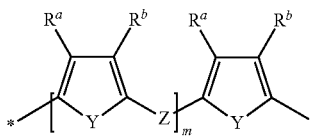

6 wherein $R^a$, $R^b$ and Y are as defined in formulae 3 and 4,
Z is —C(T$^1$)=C(T$^2$)-, —C≡C—, —N(R$^f$)—, —N=N—, (R$^f$)=N—, —N=C(R$^f$)—,
T$^1$ and T$^2$ independently of each other denote H, Cl, F, —CN or lower alkyl with 1 to 8 C atoms,
R$^f$ is H or optionally substituted alkyl or aryl;

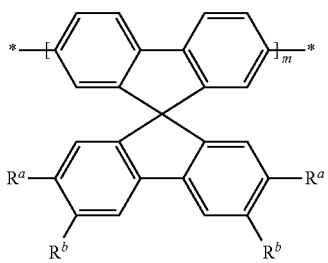

7 wherein $R^a$ and $R^b$ are as defined in formula 3;

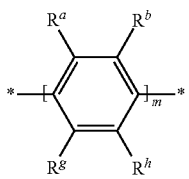

8 wherein $R^a$, $R^b$, $R^g$ and $R^h$ independently of each other have one of the meanings of $R^a$ and $R^b$ in formula 3.

In the case of the polymeric formulae described herein, such as formulae 1 to 8, the polymers may be terminated by any terminal group, that is any end-capping or leaving group, including H.

In the case of a block-copolymer, each monomer A, B, ... Z may be a conjugated oligomer or polymer comprising a number, for example 2 to 50, of the units of formulae 3-8. The semiconducting binder preferably includes: arylamine, fluorene, thiophene, spirobifluorene and/or optionally substituted aryl (for example phenylene) groups, more preferably arylamine, most preferably triarylamine groups. The aforementioned groups may be linked by further conjugating groups, for example vinylene.

In addition, it is preferred that the semiconducting binder comprises a polymer (either a homo-polymer or copolymer, including block-copolymer) containing one or more of the aforementioned arylamine, fluorene, thiophene and/or optionally substituted aryl groups. A preferred semi-conducting binder comprises a homo-polymer or copolymer (including block-copolymer) containing arylamine (preferably tri-arylamine) and/or fluorene units. Another preferred semiconducting binder comprises a homo-polymer or co-polymer (including block-copolymer) containing fluorene and/or thiophene units.

The semiconducting binder may also contain carbazole or stilbene repeat units. For example, polyvinylcarbazole, polystilbene or their copolymers may be used. The semiconducting binder may optionally contain DBBDT segments (for example repeat units as described for formula 1 above) to improve compatibility with the soluble compounds of formula.

Very preferred semiconducting binders for use in the organic semiconductor formulation according to the present invention are poly(9-vinylcarbazole) and PTAA1, a polytriarylamine of the following formula

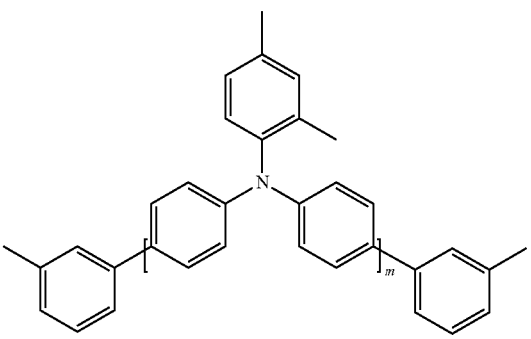

wherein m is as defined in formula 1.

For application of the semiconducting layer in p-channel FETs, it is desirable that the semiconducting binder should have a higher ionisation potential than the semiconducting compound of formula I, otherwise the binder may form hole traps. In n-channel materials the semiconducting binder should have lower electron affinity than the n-type semiconductor to avoid electron trapping.

The formulation according to the present invention may be prepared by a process which comprises:
(i) first mixing a compound of formula I and an organic binder or a precursor thereof. Preferably the mixing comprises mixing the two components together in a solvent or solvent mixture,
(ii) applying the solvent(s) containing the compound of formula I and the organic binder to a substrate; and optionally evaporating the solvent(s) to form a solid organic semiconducting layer according to the present invention,
(iii) and optionally removing the solid layer from the substrate or the substrate from the solid layer.

In step (i) the solvent may be a single solvent or the compound of formula I and the organic binder may each be dissolved in a separate solvent followed by mixing the two resultant solutions to mix the compounds.

The binder may be formed in situ by mixing or dissolving a compound of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound of formula I in a suitable solvent, and the solution deposited for example by dipping, spraying, painting or printing it on a substrate to form a liquid layer and then removing the solvent to leave a solid layer. It will be appreciated that solvents are chosen which are able to dissolve both the binder and the compound of formula I, and which upon evaporation from the solution blend give a coherent defect free layer.

Suitable solvents for the binder or the compound of formula I can be determined by preparing a contour diagram for the material as described in ASTM Method D 3132 at the concentration at which the mixture will be employed. The material is added to a wide variety of solvents as described in the ASTM method.

It will also be appreciated that in accordance with the present invention the formulation may also comprise two or more compounds of formula I and/or two or more binders or binder precursors, and that the process for preparing the formulation may be applied to such formulations.

Examples of suitable and preferred organic solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetralin, decalin, indane and/or mixtures thereof.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38(496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the binder and the compound of formula I, although it is desirable to have at least one true solvent in a blend.

Especially preferred solvents for use in the formulation according to the present invention, with insulating or semiconducting binders and mixtures thereof, are xylene(s), toluene, tetralin and o-dichlorobenzene.

The proportions of binder to the compound of formula I in the formulation or layer according to the present invention are typically 20:1 to 1:20 by weight, preferably 10:1 to 1:10 more preferably 5:1 to 1:5, still more preferably 3:1 to 1:3 further preferably 2:1 to 1:2 and especially 1:1. Surprisingly and beneficially, dilution of the compound of formula I in the binder has been found to have little or no detrimental effect on the charge mobility, in contrast to what would have been expected from the prior art.

In accordance with the present invention it has further been found that the level of the solids content in the organic semiconducting layer formulation is also a factor in achieving improved mobility values for electronic devices such as OFETs. The solids content of the formulation is commonly expressed as follows:

$$\text{Solids content } (\%) = \frac{a+b}{a+b+c} \times 100$$

wherein a=mass of compound of formula I, b=mass of binder and c=mass of solvent.

The solids content of the formulation is preferably 0.1 to 10% by weight, more preferably 0.5 to 5% by weight.

Surprisingly and beneficially, dilution of the compound of formula I in the binder has been found to have little or no effect on the charge mobility, in contrast to what would have been expected from the prior art.

The compounds according to the present invention can also be used in mixtures or blends, for example together with other compounds having charge-transport, semiconducting, electrically conducting, photoconducting and/or light emitting semiconducting properties. Thus, another aspect of the invention relates to a mixture or blend comprising one or more compounds of formula I and one or more further compounds having one or more of the above-mentioned properties. These mixtures can be prepared by conventional methods that are described in prior art and known to the skilled person. Typically the compounds are mixed with each other or dissolved in suitable solvents and the solutions combined.

The formulations according to the present invention can additionally comprise one or more further components like for example surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

It is desirable to generate small structures in modern microelectronics to reduce cost (more devices/unit area) and power consumption. Patterning of the layer of the invention may be carried out by photolithography or electron beam lithography.

Liquid coating of organic electronic devices such as field effect transistors is more desirable than vacuum deposition techniques. The formulations of the present invention enable the use of a number of liquid coating techniques. The organic semiconductor layer may be incorporated into the final device structure by, for example and without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. The present invention is particularly suitable for use in spin coating the organic semiconductor layer into the final device structure.

Selected formulations of the present invention may be applied to prefabricated device substrates by ink jet printing or microdispensing. Preferably, industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the mixture of the compound of formula I and the binder should be first dissolved in a suitable solvent. Solvents must fulfil the requirements stated above and must not have any detrimental effect on the chosen print head.

Additionally, solvents should have boiling points >100° C., preferably >140° C. and more preferably >150° C. in order to prevent operability problems caused by the solution drying out inside the print head. Suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a formulation according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the binder and the compound of formula I which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1 to 100 mPa·s, more preferably 1 to 50 mPa·s and most preferably 1 to 30 mPa·s.

The use of the binder in the present invention allows tuning the viscosity of the coating solution, to meet the requirements of particular print heads.

The semiconducting layer of the present invention is typically at most 1 micron (=1 µm) thick, although it may be thicker if required. The exact thickness of the layer will depend, for example, upon the requirements of the electronic device in which the layer is used. For use in an OFET or OLED, the layer thickness may typically be 500 nm or less.

In the semiconducting layer of the present invention there may be used two or more different compounds of formula I. Additionally or alternatively, in the semiconducting layer there may be used two or more organic binders of the present invention.

As mentioned above, the invention further provides a process for preparing the organic semiconducting layer which comprises (i) depositing on a substrate a liquid layer of a formulation which comprises one or more compounds of formula I, one or more organic binders or precursors thereof and optionally one or more solvents, and (ii) forming from the liquid layer a solid layer which is the organic semiconducting layer.

In the process, the solid layer may be formed by evaporation of the solvent and/or by reacting the binder resin precursor (if present) to form the binder resin in situ. The substrate may include any underlying device layer, electrode or separate substrate such as silicon wafer or polymer substrate for example.

In a particular embodiment of the present invention, the binder may be alignable, for example capable of forming a liquid crystalline phase. In that case the binder may assist alignment of the compound of formula I, for example such that their aromatic core is preferentially aligned along the direction of charge transport. Suitable processes for aligning the binder include those processes used to align polymeric organic semiconductors and are described in prior art, for example in US 2004/0248338 A1.

The formulation according to the present invention can additionally comprise one or more further components like for example surface-active compounds, lubricating agents, wetting agents, dispersing agents, hydrophobing agents, adhesive agents, flow improvers, defoaming agents, deaerators, diluents, reactive or non-reactive diluents, auxiliaries, colourants, dyes or pigments, furthermore, especially in case crosslinkable binders are used, catalysts, sensitizers, stabilizers, inhibitors, chain-transfer agents or co-reacting monomers.

The present invention also provides the use of the semiconducting compound, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising the formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compounds and formulations according to the present invention are useful as charge transport, semiconducting, electrically conducting, photoconducting or light mitting materials in optical, electrooptical, electronic, electroluminescent or photoluminescent components or devices. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns. In these devices, the compounds of the present invention are typically applied as thin layers or films.

For example, the compound or formulation may be used as a layer or film, in a field effect transistor (FET) for example as the semiconducting channel, organic light emitting diode (OLED) for example as a hole or electron injection or transport layer or electroluminescent layer, photodetector, chemical detector, photovoltaic cell (PVs), capacitor sensor, logic circuit, display, memory device and the like. The compound or formulation may also be used in electrophotographic (EP) apparatus.

The compound or formulation is preferably solution coated to form a layer or film in the aforementioned devices or apparatus to provide advantages in cost and versatility of manufacture. The improved charge carrier mobility of the compound or formulation of the present invention enables such devices or apparatus to operate faster and/or more efficiently.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a compound of formula I according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G.

Yu, J. Gao, J. C. Hummelen, F. Wudl, A. J. Heeger, *Science* 1995, 270, 1789 ff and having the structure shown below, or an structural analogous compound with e.g. a $C_{70}$ fullerene group ($C_{70}$PCBM), or a polymer (see for example Coakley, K. M. and McGehee, M. D. *Chem. Mater.* 2004, 16, 4533).

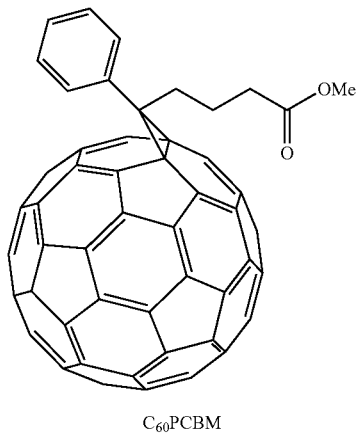 [SMILES: COC(=O)CCCC1(c2ccccc2)C23C=C4CC5=CC6C=C7Cc8cc9cc%10c%11c(c%12c%13c%14c(c4c5c4c%14c5c(c7c8c7c9c%11c%13c57)C46)C%1221)C(=C3)C%10]

$C_{60}$PCBM

A preferred material of this type is a blend or mixture of an acene compound of formula I according to the present invention with a $C_{60}$ or $C_{70}$ fullerene or modified fullerene like PCBM. Preferably the ratio acene:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature (see for example Waldauf et al., Appl. Phys. Lett. 89, 233517 (2006), or Coakley, K. M. and McGehee, M. D. *Chem. Mater.* 2004, 16, 4533).

A first preferred OPV device according to the invention comprises the following layers (in the sequence from bottom to top):
  a high work function electrode preferably comprising a metal oxide like for example ITO, serving as anode,
  an optional conducting polymer layer or hole transport layer, preferably comprising an organic poymer or polymer blend, for example of PEDOT:PSS (poly(3,4-ethylenedioxythiophene): poly(styrene-sulfonate),
  a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF,
  a low work function electrode, preferably comprising a metal like for example aluminum, serving as cathode,
  wherein at least one of the electrodes, preferably the anode, is transparent to visible light, and
  wherein the p-type semiconductor is a compound of formula I according to the present invention.

A second preferred OPV device according to the invention is an inverted OPV device and comprises the following layers (in the sequence from bottom to top):
  an electrode comprising for example ITO serving as cathode,
  optionally a layer having hole blocking properties, preferably comprising a metal oxide like $TiO_x$ or $Zn_x$,
  an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic poymer or polymer blend, for example of PEDOT:PSS,
  a high work function electrode, preferably comprising a metal like for example gold, serving as anode,
  wherein at least one of the electrodes, preferably the cathode, is transparent to visible light, and
  wherein the p-type semiconductor is a compound of formula I according to the present invention.

In the OPV devices of the present invent invention the p-type and n-type semiconductor materials are preferably selected from the materials, like the acenefullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound of formula I, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
wherein the semiconductor layer preferably comprises a compound of formula I or a formulation according to the present invention.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al., Synth. Metals, 2000, 111-112, 31, Alcala, *J. Appl. Phys.*, 2000, 88, 7124 and the literature cited therein.

According to another use, the materials according to this invention, especially those showing photoluminescent properties, may be employed as materials of light sources, e.g. in display devices, as described in EP 0 889 350 A1 or by C. Weder et al., *Science*, 1998, 279, 835.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, ($R$ is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention amy also be suitable for use in organic plasmon-emitting diodes (OPEDs), as described for example in Koller et al., Nat. Photonics, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use, the materials according to the present invention, especially their water-soluble derivatives (for example with polar or ionic side groups) or ionically doped forms, can be employed as chemical sensors or materials for detecting and discriminating DNA sequences.

Such uses are described for example in L. Chen, D. W. McBranch, H. Wang, R. Helgeson, F. Wudl and D. G. Whitten, *Proc. Natl. Acad. Sci. U.S.A.* 1999, 96, 12287; D. Wang, X. Gong, P. S. Heeger, F. Rininsland, G. C. Bazan and A. J. Heeger, *Proc. Natl. Acad. Sci. U.S.A.* 2002, 99, 49; N. DiCesare, M. R. Pinot, K. S. Schanze and J. R. Lakowicz, *Langmuir* 2002, 18, 7785; D. T. McQuade, A. E. Pullen, T. M. Swager, *Chem. Rev.* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

Unless stated otherwise, above and below percentages are per cent by weight and temperatures are given in degrees Celsius.

EXAMPLE 1

5,9,14,18-tetrakis[(triethylsilyl)ethynyl]indanthrene

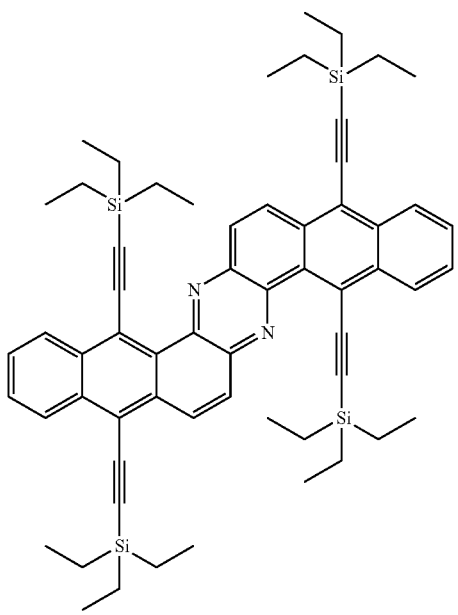 [SMILES: CC[Si](C#Cc1c2ccccc2c(C#C[Si](CC)(CC)CC)c2c1ccc1nc3c(ccc4c(C#C[Si](CC)(CC)CC)c5ccccc5c(C#C[Si](CC)(CC)CC)c43)nc12)(CC)CC]

To a solution of triethylethynylsilane (2.245 g; 16.00 mmol) in dioxane (anhydrous, 30 cm$^3$) was added at 0° C. n-BuLi (2.5M in hexanes, 6.4 cm$^3$; 16.00 mmol) over 5 minutes to yield an off-white suspension. The cooling bath was removed and the solution was stirred at 22° C. for an additional 30 minutes. Indanthrene-5,9,14,18-tetraone (0.881 g; 2.00 mmol) was added in one portion and the dark green mixture was sonicated for ca. 2 minutes then stirred at 22° C. for 60 hours to yield a brown solution.

Saturated NH$_4$Cl solution (30 cm$^3$) was added and the mixture was stirred at 22° C. for 1 hour. The upper brown organic layer was separated and suction filtered to remove the insoluble impurities. The filtrate was vacuum evaporated. The brown oil residue was mixed with acetic acid (30 cm$^3$), KI (1.660 g; 10.00 mmol) and sodium hypophosphite (0.880 g; 10.00 mmol). The mixture was stirred at 120° C. (external) for 40 minutes to yield a brown solution.

The solution was cooled with an ice-water bath followed by the addition of NH$_4$Cl solution (30 cm$^3$). The brown precipitated was taken into chloroform (2×25 cm$^3$) and the yellow-brown chloroform solution was dried over magnesium sulfate. The solution was concentrated to dryness then flash chromatographed on silica (3:2 v/v cyclohexane-chloroform) to yield a yellow powdery solid. The solid was recrystallised from chloroform-IMS to afford yellow crystals 0.93 g (50%). M.p.=296° C. (DSC). $^1$H NMR (CDCl$_3$, 300 MHz): δ=0.92 (q, 6.0 Hz, 6H), 0.98 (q, 6.0 Hz, 6H), 1.24 (m, 18H), 7.79 (m, 2H), 8.20 (d, 6.0 Hz, 1H), 8.73 (m, 1H), 8.84 (d, 6.0 Hz, 1H), 9.08 (m, 1H).

EXAMPLE 2

5,9,14,18-tetrakis[(cyclopentyldiethylsilyl)ethynyl] indanthrene

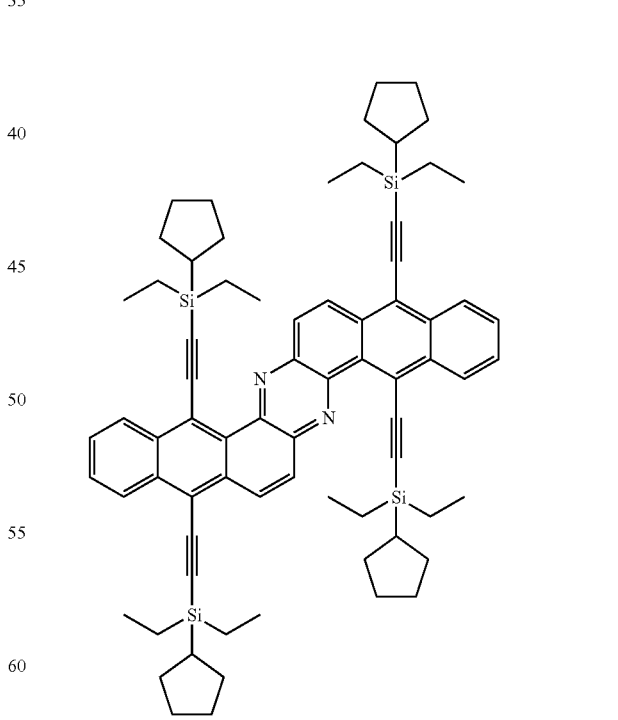

To a solution of cyclopentyldiethylethynylsilane (3.313 g; 16.00 mmol) in anhydrous dioxane (30 cm$^3$) was added at 0° C. n-BuLi (2.5M in hexanes, 6.4 cm$^3$; 16.00 mmol) dropwise over 5 minutes to yield a pale-yellow solution. The cooling bath was removed and the solution was stirred at 22° C. for an additional 30 minutes. Indanthrene-5,9,14,18-tetraone (0.881 g; 2.00 mmol) was added in one portion and the dark green mixture was sonicated for ca. 2 minutes then stirred at 22° C. for 20 hours to yield a brown solution. The solution was then stirred at 50° C. (external) for 5.5 hours and at 22° C. again for an additional 50 hours.

Saturated $NH_4Cl$ solution (30 cm³) was added and the mixture was stirred at 22° C. for 10 minutes. The upper brown organic layer was separated and suction filtered to remove the insoluble impurities. The filtrated was vacuum evaporated and the brown oil residue was mixed with acetic acid (30 cm³), KI (1.660 g; 10.00 mmol) and sodium hypophosphite (0.880 g; 10.00 mmol). The mixture was stirred at 120° C. (external) for 1 hour to yield a brown solution. The solution was cooled to 22° C. followed by the addition of $NH_4Cl$ solution (30 cm³). The brown precipitated was taken into chloroform (2×30 cm³). The solution was concentrated to dryness then flash-columned on silica (3:2 cyclohexane-chloroform) to yield a yellow solid, which crystallised from chloroform-IMS mixture to yield golden yellow plates (0.436 g, 20%). M.p.=320.4° C. (DSC). $^1$H NMR ($CDCl_3$, 300 MHz): δ=0.99 (m, 8H), 1.26 (m, 14H), 1.72 (m, 12H), 2.01 (m, 4H), 7.77 (m, 2H), 8.21 (d, 6.0 Hz, 1H), 7.74 (m, 1H), 8.85 (d, 6.0 Hz, 1H), 9.10 (m, 1H).

EXAMPLE 3

5,9,14,18-tetrakis[(cyclohexyldimethylsilyl)ethynyl]indanthrene

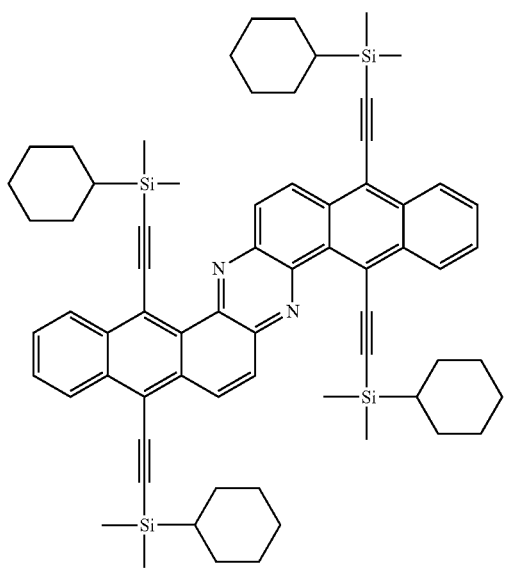 [SMILES: C[Si](C)(C#Cc1c2ccccc2c(C#C[Si](C)(C)C2CCCCC2)c2c1ccc1nc3c(ccc4c(C#C[Si](C)(C)C5CCCCC5)c5ccccc5c(C#C[Si](C)(C)C5CCCCC5)c43)nc12)C1CCCCC1]

To the solution of cyclohexylethynyldimethylsilane (3.001 g; 17.50 mmol;) in dioxane (anhydrous, 30 cm³) was added at 0° C. n-BuLi (7.0 cm³; 17.50 mmol) dropwise within 5 min to yield an off-white suspension. The cooling bath was removed and the solution was stirred at 20° C. for an additional 30 min. The suspension turned into a pale-yellow clear solution.

Indanthrene-5,9,14,18-tetraone (0.881 g; 2.00 mmol) was added in one portion as solid and the dark green mixture was supersonicated for ca 2 min then stirred at 20° C. for 50 h at 50° C. (external) for an additional 5 h to yield a brown solution.

Saturated ammonium chloride solution (50 cm³) was added and the mixture was stirred at 20° C. for 30 min. The upper brown organic layer was separated and the aqueous layer was extracted with diethyl ether (30 cm³) once. The combined ether solution was dried over $MgSO_4$ and suction filtered. The filtrated was vacuum evaporated to yield a brown stick solid. The solid was mixed with acetic acid (30 cm³), potassium iodide (1.660 g; 10.00 mmol) and $NaH_2PO_2 \cdot H_2O$ (1.060 g; 10.00 mmol). The mixture was stirred at 120° C. (external) for 1 h. The solution was cooled naturally to 20° C. followed by the addition of water (50 cm³). The brown precipitate was suction filtered off and washed with methanol, to yield a dark brown solid, which was flash columned on silica washed with 2:1 cyclohexane-chloroform to yield the product as a yellow solid (0.78 g, 37%). M.p.=234.7° C. (DSC). $^1$H NMR ($CDCl_3$, 300 MHz): δ=0.40 (s, 6H), 0.47 (s, 6H), 1.00 (m, 2H), 1.35 (m, 12H), 1.79 (m, 6H), 2.00 (m, 4H), 7.80 (m, 2H), 8.20 (d, 9 Hz, 1H), 8.72 (m, 1H), 8.83 (d, 9 Hz, 1H), 9.05 (m, 1H).

EXAMPLE 4

Transistor Fabrication and Measurement

Top-gate thin-film organic field-effect transistors (OFETs) were fabricated on glass substrates with thermally evaporated Au or Ag source-drain electrodes. A 2 wt. % solution of each compound (solvent see Table 1) was spin-coated on the top. The film was annealed at 100° C. for 60 seconds. Next a fluoropolymer dielectric material (D139) was spin-coated. Finally a Au gate electrode was deposited by thermal evaporation. The electrical characterization of the transistor devices was carried out in ambient air atmosphere using computer controlled Agilent 4155C Semiconductor Parameter Analyser. Charge carrier mobility in the saturation regime ($\mu_{sat}$) was calculated for the compound and the results are summarized in Table 1. Field-effect mobility was calculated in the saturation regime ($V_d > (V_g - V_0)$) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

TABLE 1

Mobilties ($\mu_{sat}$) for Examples 1 and 3 in top-gate OFETs.

| Example | Solvent | Electrode | Mobility ($\mu_{sat}$)/cm²/Vs |
|---------|-----------|-----------|-------------------------------|
| 1       | mesitylene | Au       | $1.2 \times 10^{-3}$         |
| 3       | mesitylene | Ag       | $1.0 \times 10^{-3}$         |

The invention claimed is:

1. A compound of formula I

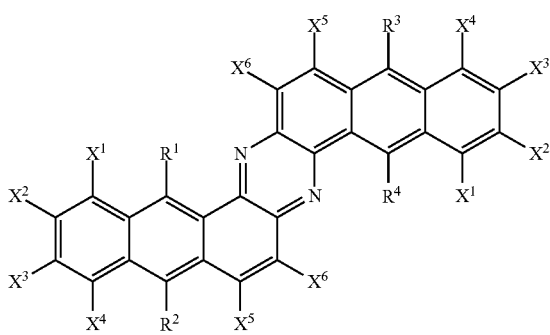

wherein
R¹ to R⁴ independently of each other denote —C≡C—R⁵
R⁵ is an optionally substituted alkyl, silyl or germyl group, or an aryl or heteroaryl group with 1 to 20 ring atoms which is unsubstituted or substituted by one or more groups L, X¹ to X⁶ independently of each other, and on each occurrence identically or differently, denote H or have one of the meanings given for L,
L is P-Sp-, F, Cl, Br, I, —OH, —CN, —NO₂, —NCO, —NCS, —OCN, —SCN, —C(=O)NR⁰R⁰⁰, —C(=O)X⁰, —C(=O)R⁰, —NR⁰R⁰⁰, C(=O)OH, optionally substituted silyl or germyl, optionally substituted aryl or heteroaryl having 4 to 20 ring atoms, straight chain, branched or cyclic alkyl, alkoxy, oxaalkyl or thioalkyl with 1 to 20 C atoms which is unsubstituted or substituted with one or more F or Cl atoms or OH groups, or straight chain, branched or cyclic alkenyl, alkynyl, alkylcarbonyl, alkoxycarbonyl, alkylcarbonyloxy or alkoxycarbonyloxy with 2 to 30 C atoms which is unsubstituted or substituted with one or more F or Cl atoms or OH groups,
P is a polymerisable group,
Sp is a spacer group or a single bond,
X⁰ is halogen, and
R⁰, R⁰⁰ independently of each other denote H or alkyl with 1 to 20 C-atoms.

2. The compound according to claim 1, wherein R⁵ is a substituted alkyl, silyl or germyl group, or an aryl or heteroaryl group with 1 to 20 ring atoms which is unsubstituted or substituted by one or more groups L.

3. The compound according to claim 1, wherein R⁵ is of formula II

-AR'R''R''' <span>II</span> wherein
A is C, Si or Ge,
R', R'', R''' are, identical or different, H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L', and
L' has one of the meanings given for L in formula I, which is different from a silyl and germyl group.

4. The compound according to claim 1, wherein X¹, X², X³, X⁴, X⁵ and X⁶ are H.

5. The compound according to claim 1, wherein X¹, X², X³, X⁴, X⁵ and X⁶ are, each independently, H, F, Cl, Br, I, —CN, or straight chain, branched or cyclic alkyl, alkoxy, thioalkyl, alkenyl, alkynyl, alkylcarbonyl, alkoxycarbonyl, alkylcarbonyloxy, alkylcarbonylamido, alkylamidocarbonyl or alkoxycarbonyloxy with 1 to 20 C atoms which is unsubstituted or substituted with one or more F or Cl atoms or OH groups or is perfluorinated, or an aromatic or heteroaromatic group with 4 to 25 ring atoms, which is mono- or polycyclic, which contains two or more individual rings that are connected to each other via single bonds, or contains two or more fused rings, and wherein each ring is unsubstituted or substituted with one or more groups L.

6. A compound of formula II

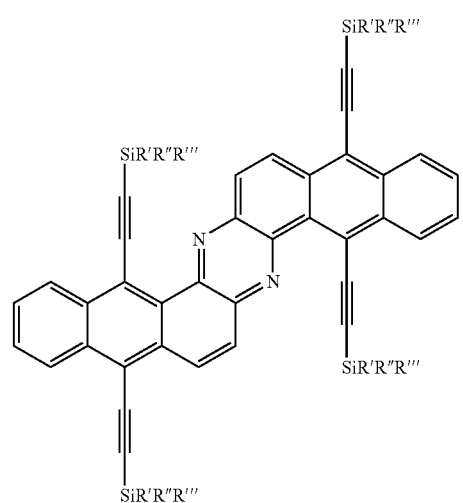

wherein
R', R'', R''' are, identical or different, H, a straight-chain, branched or cyclic alkyl or alkoxy group having 1 to 20 C atoms, a straight-chain, branched or cyclic alkenyl group having 2 to 20 C atoms, a straight-chain, branched or cyclic alkynyl group having 2 to 20 C atoms, a straight-chain, branched or cyclic alkylcarbonyl group having 2 to 20 C atoms, an aryl or heteroaryl group having 4 to 20 ring atoms, an arylalkyl or heteroarylalkyl group having 4 to 20 ring atoms, an aryloxy or heteroaryloxy group having 4 to 20 ring atoms, or an arylalkyloxy or heteroarylalkyloxy group having 4 to 20 ring atoms, wherein all the aforementioned groups are optionally substituted with one or more groups L',
L' is P-Sp-, F, Cl, Br, I, —OH, —CN, —NO₂, —NCO, —NCS, —OCN, —SCN, —C(=O)NR⁰R⁰⁰, —C(=O)X⁰, —C(=O)R⁰R⁰⁰, C(=O)OH, optionally substituted aryl or heteroaryl having 4 to 20 ring atoms, straight chain, branched or cyclic alkyl, alkoxy, oxaalkyl or thioalkyl with 1 to 20-C atoms which is unsubstituted or substituted with one or more F or Cl atoms or OH groups, or straight chain, branched or cyclic alkenyl, alkynyl, alkylcarbonyl, alkoxycarbonyl, alkylcarbonyloxy or alkoxycarbonyloxy with 2 to 30 C atoms which is unsubstituted or substituted with one or more F or Cl atoms or OH groups, P is a polymerisable group, Sp is a spacer group or a single bond, $X^0$ is halogen, and $R^0$, $R^{00}$ independently of each other denote H or alkyl with 1 to 20 C-atoms.

7. A formulation comprising one or more compounds according to claim 1 and one or more organic solvents.

8. A formulation comprising one or more compounds according to claim 1, one or more organic binders or precursors thereof, optionally having a permittivity ∈ at 1,000 Hz of 3.3 or less, and optionally one or more solvents.

9. A charge transport, semiconducting, electrically conducting, photoconducting or light emitting material or component comprising one or more compounds according to claim 1.

10. An optical, electrooptical, electronic, electroluminescent or photoluminescent component or device comprising one or more compounds according to claim 1.

11. The component or device according to claim 10, which is selected from the group consisting of organic field effect transistors (OFET), thin film transistors (TFT), integrated circuits (IC), logic circuits, capacitors, radio frequency identification (RFID) tags, radio frequency identification (RFID) devices, radio frequency identification (RFID) components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers in polymer light emitting diodes (PLEDs), charge transport interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, components for detecting and discriminating DNA sequences, and devices for detecting and discriminating DNA sequences.

12. The compound according to claim 3, wherein A is Si.

13. A formulation comprising one or more compounds according to claim 6 and one or more organic solvents.

14. A formulation comprising one or more compounds according to claim 6, one or more organic binders or precursors thereof, optionally having a permittivity ∈ at 1,000 Hz of 3.3 or less, and optionally one or more solvents.

15. A charge transport, semiconducting, electrically conducting, photoconducting or light emitting material or component comprising one or more compounds according to claim 6.

16. An optical, electrooptical, electronic, electroluminescent or photoluminescent component or device comprising one or more compounds according to claim 6.

17. The component or device according to claim 16, which is selected from the group consisting of organic field effect transistors (OFET), thin film transistors (TFT), integrated circuits (IC), logic circuits, capacitors, radio frequency identification (RFID) tags, radio frequency identification (RFID) devices, radio frequency identification (RFID) components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers in polymer light emitting diodes (PLEDs), charge transport interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, components for detecting and discriminating DNA sequences, and devices for detecting and discriminating DNA sequences.

\* \* \* \* \*